United States Patent [19]
Garlich et al.

[11] Patent Number: 5,133,956
[45] Date of Patent: Jul. 28, 1992

[54] RADIOLABELED METAL-BINDING PROTEIN FOR THE TREATMENT OF ARTHRITIS

[75] Inventors: Joseph R. Garlich, Lake Jackson; Kenneth McMillan, Richwood; Jaime Simon, Angleton, all of Tex.

[73] Assignee: The Dow Chemical Company, Midland, Mich.

[21] Appl. No.: 707,719

[22] Filed: May 30, 1991

[51] Int. Cl.$^5$ .......................... A61K 43/00; C07F 5/00
[52] U.S. Cl. ..................... 424/1.1; 534/15; 534/10; 252/625
[58] Field of Search ............... 252/625; 534/10, 15; 424/1.1

[56] References Cited

U.S. PATENT DOCUMENTS

| | | | |
|---|---|---|---|
| 3,663,685 | 5/1972 | Evans | 424/1 |
| 4,104,366 | 8/1978 | Schmidt-Dunker et al. | 424/1 |
| 4,454,106 | 6/1984 | Gansow et al. | 424/1.1 |
| 4,622,420 | 11/1986 | Meares et al. | 562/443 |
| 4,752,464 | 6/1988 | Lieberman et al. | 424/1.1 |
| 4,758,429 | 7/1988 | Gordon | 424/85 |
| 4,849,209 | 7/1989 | Lieberman et al. | 424/1.1 |
| 4,853,209 | 8/1989 | Kaplan et al. | 424/1.1 |
| 4,882,142 | 11/1989 | Simon et al. | 424/1.22 |
| 4,889,707 | 12/1989 | Day et al. | 424/1.1 |
| 4,897,254 | 1/1990 | Simon et al. | 424/1.1 |
| 4,898,724 | 2/1990 | Simon et al. | 424/1.1 |
| 4,906,450 | 3/1990 | Lieberman et al. | 424/1.1 |
| 4,915,932 | 4/1990 | McLaren et al. | 424/1.1 |
| 4,970,062 | 11/1990 | Atcher et al. | 424/1.1 |
| 4,976,950 | 12/1990 | Simon et al. | 424/1.1 |
| 5,021,236 | 6/1991 | Gries et al. | 424/1.1 X |
| 5,032,678 | 7/1991 | Washino et al. | 534/14 |
| 5,037,630 | 8/1991 | Fritzberg et al. | 424/1.1 |
| 5,039,326 | 8/1991 | Day et al. | 424/1.1 X |

OTHER PUBLICATIONS

C. B. Sledge et al., "Experimental Radiation Synovectomy by 165 Dy Ferric Hydroxide Macroaggregate", *Arthritic and Rheumatism*, 20, pp. 1334–1342.

C. B. Sledge et al., "Intra-articular Radiation Synovectomy", *Clinical Orthopedics and Related Research*, 182, pp. 37–40 (1984).

C. B. Sledge et al., "Treatment of Rheumatoid Synovitis of the Knee with Intra-articular . . . ", *Arthritis and Rheumatism*, 29, pp. 153–159 (1986).

L. K. Doepel, "Radionuclide Therapy for Arthritic Knees", *J.A.M.A.*, 253, pp. 744–745 (1985).

P.F.M.J. Spooren et al., "Synovectomy of the Knee with 90 Y", *Nuclear Medicine*, pp. 441–445, (1985).

L. Rosenthall, "Use of Radiocolloids for Intra-articular Therapy for Synovitis", *Therapy in Nuclear Medicine*, pp. 147–242 (1978).

D. J. Hnatowich et al., "Dysprosium-165 Ferric Hydroxide Macroaggregates for Radiation Synovectomy", *J. Nuclear Medicine*, 19, pp. 303–308.

*Primary Examiner*—Robert L. Stoll
*Assistant Examiner*—C. Sayala

[57] ABSTRACT

Radioactive high molecular weight metal-binding protein compositions and a method for therapeutic radiation treatment including the treatment of rheumatoid arthritis comprising injection of a radioactive high molecular weight metal-binding protein compositions are disclosed.

16 Claims, No Drawings

RADIOLABELED METAL-BINDING PROTEIN FOR THE TREATMENT OF ARTHRITIS

FIELD OF THE INVENTION

This invention relates to radioactive high molecular weight metal-binding protein compositions and to a method for the treatment of rheumatoid arthritis by administering such radioactive high molecular weight metal-binding protein compositions.

BACKGROUND OF THE INVENTION

Rheumatoid arthritis is a prevalent disease characterized by chronic inflammation of the synovial membrane lining the afflicted joint. Current treatment methods for severe cases of rheumatoid arthritis include the removal of the synovial membrane, e.g., synovectomy. Surgical synovectomy has many limitations including the risk of the surgical procedure itself, and the fact that a surgeon often cannot remove all of the membrane. The diseased tissue remaining may eventually regenerate, causing the same symptoms which the surgery was meant to alleviate.

Radiation synovectomy is radiation-induced ablation of diseased synovial membrane tissue accomplished by injecting a radioactive compound into the diseased synovium. Early attempts to perform radiation synovectomy were hampered by an instability of the radioactive compounds utilized and by leakage of such compounds from the synovium into surrounding healthy tissues. The instability of labile radionuclide-complexes resulted in displacement of the radionuclide from the colloid complex and retention of the radionuclide in soft tissues. Significant leakage of the radioactive compound from the injection site exposed normal tissues to dangerous levels of radiation. Because of these limitations, new radiolabeled compositions were sought which would have minimal leakage.

U.S. Pat. No. 4,752,464 describes a composition comprising a radioactive colloid in which a radionuclide is entrapped within an iron hydroxide matrix. Radioactive colloids are useful in radiation ablation procedures, for example, ablation of a synovium in rheumatoid arthritis; however, their use may still result in significant leakage of radioactivity from a site of injection, e.g., a synovium, and into the surrounding normal tissues, exposing normal tissues to an undesirable amount of radiation. To compensate for the leakage, a radioactive metal having a short half-life, such as Dysprosium (Dy-165) with a half-life of 2.3 hours has been proposed for use as the labeling radionuclide. Because of its short half-life, the majority of Dy-165 radioactivity decays before significant leakage can occur, thereby minimizing the dose of radiation seen by normal tissues.

The use of radioactive metals having a short half-life severely limits the utility of the therapeutic radiation procedure in two significant ways. First, radioactive compositions prepared with short half-life isotopes lose a significant amount of radioactivity because of decay during shipment to distant locations. Second, to achieve a therapeutic dose of a composition comprising a radioactive metal having a short half-life, large amounts of radioactive materials must be used. As a result, clinical personnel must handle large amounts of radioactive materials.

Therefore, there remains a need for a therapeutic radioactive composition which upon injection into a synovium, would remain at the site of injection, e.g., within a synovium, for a prolonged period of time. Prolonged retention at the site of injection would allow use of radionuclides having a longer half-life in therapeutic procedures, including radiation synovectomy, without fear of significant leakage from the site of injection and radiation exposure to normal tissues.

SUMMARY OF THE INVENTION

It has now been found that when radioactive compositions prepared from radionuclides and high molecular weight metal-binding proteins are injected into a synovium, they are retained at the site of injection for a prolonged period of time, without significant leakage of radioactivity. Radioactive compositions prepared from high molecular weight metal-binding proteins may be prepared with radionuclides having longer half-lives than previously used in radiation ablation procedures, greatly minimizing fear of significant leakage from the site of injection and radiation exposure to normal tissues.

DETAILED DESCRIPTION OF THE INVENTION

The compositions of the present invention include high molecular weight metal-binding proteins complexed with therapeutic radionuclides. The preferred metal-binding proteins are those having a high molecular weight as determined in the absence of bound metals, preferably those having a molecular weight of greater than 50,000, more preferably greater than 100,000 and most preferably greater than 250,000.

In the phrase "metal-binding protein", the word "metal" designates a metal cation wherein a portion of the metal is radioactive. The term "metal-binding protein" designates a protein which naturally possesses the ability to bind metal cations; the term "binding" means an attraction between the protein and metal cation, including covalent or ionic bonding, which can be measured by standard techniques after mixing the protein and metal cation in an aqueous solution, such as separation of proteins containing metal cations from nonmetal binding proteins by gel permeation chromatography, dialysis, ion exchange chromatography, electrophoresis, high performance liquid chromatography or thin layer chromatography. The term "metal-binding protein" also designates a protein which has been modified by the conjugation of a metal chelating ligand to said protein. The word "protein" includes proteins containing only amino acids connected by peptide linkages and conjugated proteins containing amino acids plus nucleic acids, carbohydrates or lipids. The metal-binding protein is preferably inert to having the metal separate from the protein when used in vivo.

Biodegradation of the protein will occur over time; but the metal does not readily leach from the protein during the desired treatment time.

Examples of preferred high molecular weight metal-binding proteins include ferritin, transferrin, hemoglobin, ceruloplasmin, hemocyanin, and the like proteins which can inherently bind metal cations, as well as proteins modified by the addition of a bifunctional chelator to impart metal-binding capability to the protein. An example of a preferred metal-binding protein is ferritin, an iron storage protein having an approximate molecular weight of 460,000 in the absence of bound metals. Ferritin contains a central structural core capable of binding as many as 4500 ferric atoms per molecule.

The preferred high molecular weight metal-binding proteins of the present invention also include high molecular weight proteins, such as immunoglobulins, which have been modified to impart metal-binding capability by the addition of a bifunctional chelator. The addition of a bifunctional chelator renders the protein capable of stably binding metals.

A bifunctional chelator is a chemical compound that has a metal chelating moiety, which is capable of sequestering or chelating metals, and a reactive group by which the compound is covalently coupled to a protein. Bifunctional chelators for use in the present invention are those that contain polyaminocarboxylates or polyaminophosphonates as the metal chelating moiety. Preferred are bifunctional chelators which contain cyclic polyaminocarboxylates or cyclic polyaminophosphonates, such as macrocyclic hetero rings of 12 to 16 total atoms in the ring.

Example of compounds known in the art which can be activated and function as bifunctional chelators according to the present invention include substituted 1,4,7-tris-carboxymethyl-1,4,7,10-tetraazacyclododecane and analogs disclosed in published European Patent Application 292689, 2-(p-nitrobenzyl)-1,4,7,10-tetraazacyclododecane-N,N',N'',N'''-tetraacetic acid disclosed in *J. Am. Chem. Soc.* 11, 6206–6207 (1988); PA-DOTA ($\alpha$-[2-(4-aminophenyl)ethyl]-1,4,7,10-tetraazacyclododecane-1,4,7,10-tetraacetic acid), PA-DOTMA ($\alpha$-[2-(4-aminophenyl)ethyl]-1,4,7,10-tetraazacyclododecane-1-acetic-4,7,10-tris(methylacetic acid), BA-DOTA ($\alpha$-(4-aminophenyl)-1,4,7,10-tetraazacyclododecane-1,4,7,10-tetraacetic acid), OMe-BA-DOTA ($\alpha$-(5-amino-2-methoxyphenyl)-1,4,7,10-tetraazacylododecnae-1,4,7,10-tetraacetic acid) and EA-DO3A (1-[2-(4-aminophenyl)ethyl]-1,4,7,10-tetraazacyclododecnae-4,7,10-triacetic acid) disclosed in PCT application WO 89/12631, published Dec. 28, 1989, the disclosure of which is hereby incorporated by reference; 1,4,7,10-tetraazacyclododecane-N,N',N'',N'''-tetraacetic acid, 1,4,7,10-tetraazacyclotridecane-N,N'N'', N''''-tetraacetic acid, 1,4,8,11-tetraazacyclotetradecane-N,N'N'',N'''-tetraacetic acid and 1,5,9,13-tetraazacyclohexadecane-N,N'N'',N'''-tetraacetic acid disclosed in U.S. Pat. No. 4,678,667, the disclosure of which is hereby incorporated by reference; and derivatives of diethylenetriaminepentaacetic acid disclosed in U.S. Pat. No. 4,831,175, the disclosure of which is hereby incorporated by reference.

Polyamino phosphonates known in the art which can be activated and function as bifunctional chelators are 1,4,7,10-tetraazacyclododenace-1,4,7,10-tetramethylenephosphonic acid and analogs disclosed in U.S. Pat. No. 4,882,142, the disclosure of which is hereby incorporated by reference, and the polyamino phosphonates disclosed in U.S. patent application, Ser. No. 07/565,379, filed Aug. 9, 1990, the disclosure of which is hereby incorporated by reference; 1,3-propanediamine-N-(carboxypropyl)-N,N',N'-trimethylenephosphonic acid, ethylenediamine-N-(4-aminophenethyl)-N,N',N',-trimethylenephosphonic acid, ethylenediaminetetramethylenephosphonic acid, 1-(carboxy)ethylenediaminetetramethylenephosphonic acid, 1-(4-aminobenzyl)ethylenediaminetetramethylenephosphonic acid, N''-(4-aminophenyl)-dipropylenetriamine-N,N',N''',N''''-tetramethylenephosphonic acid and N''-(4-aminophenyl)-diethylenetriamine-N'N',N''',N''''-tetramethylenephosphonic acid being representative of the polyamine phosphonates in U.S. patent application, Ser. No. 07/565,379.

Methods for making bifunctional chelators are well known in the art. In one method, one or more carboxylic acid groups of a polyamine, polycarboxylic acid chelator are activated by conversion to such activating groups as internal or mixed anhydrides, activated esters (e.g. para-nitrophenyl, N-hydroxysuccinimide, etc.) or with other derivatives known to those skilled in the art. The activated acid group is then reacted with the protein. The metal ion is then added to the protein-chelator complex.

Another method for making a bifunctional chelator is to prepare a chelating ligand with a unique reactive group, such as an isothiocyanate, attached to the chelating moiety at a position that does not substantially diminish the strength with which the chelating ligand binds the metal ion. An article by M. W. Brechbiel et al., *Inorg. Chem.* 25, 2772–2781 (1986) is illustrative of this second procedure. Examples of other protein-binding functional groups of bifunctional chelators include electrophilic or nucleophilic moieties such as bromoacetamide, maleimide, imidoester, thiophthalimide, N-hydroxysuccinimyl ester, pyridyl disulfide, phenyl azide, o-acylisourea, anhydride, diazonium, carboxyl, amino, acyl hydrazide, semicarbazide, and thiosemicarbazide groups.

The modification of proteins by the addition of bifunctional chelators may be accomplished by methods known in the art. Generally, these methods include formation of a covalent linkage with an amino acid residue of the protein and a functional group of the bifunctional chelator which is capable of binding proteins.

Binding of a therapeutic radioactive metal to a high molecular weight protein or protein-chelator conjugate may be accomplished by exposing the metal binding protein to an aqueous solution of the metal ion, at a pH of about 3 to about 12, preferably about 4 to about 9.

The bifunctional chelator may be reacted with a therapeutic radioactive metal and the complex then attached to a protein. Alternatively, a protein may first be modified by the addition of the bifunctional chelator, and the modified protein conjugate then reacted with a therapeutic radioactive metal.

Radionuclides for use in the present invention are beta emitters with half-lives in the range of from about 2 hours to about 7 days. Preferred radionuclides are the radionuclides Holmium (Ho-166), Samarium (Sm-153), Rhodium (Rh-105), Lutetium (Lu-177), Indium (In-115 m), Dysprosium (Dy-165), Yttrium (Y-90), Lanthanum (La-140), Gadolinium (Gd-159), Ytterbium (Yb-175), Rhenium (Re-186), (Re-188) and Scandium (Sc-47). More preferred are the radionuclides Ho-166, Sm-153, Re-186, Re-188, Rh-105, Lu-177, In-115 m, and Dy-165.

The respective radionuclides can be produced by methods known in the art. For example, in a nuclear reactor, a nuclide is bombarded with neutrons to obtain a nuclide with additional neutrons in its nucleus. For example:

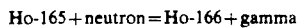

Ho-165 + neutron = Ho-166 + gamma

Typically, the desired radionuclide can be prepared by irradiating an appropriate target, such as a metal oxide. Another method of obtaining radionuclides is by bombarding nuclides with particles in a linear accelerator or cyclotron. Yet another way of obtaining radionuclides is to isolate them from fission product mixtures.

The ratio of the amount of radioactive metal to the amount of high molecular weight metal-binding protein to be used in the preparation of the compositions of the present invention will vary according to the specific protein to be radiolabeled, its specificity and metal-binding capacity. For example, the metal-binding protein, ferritin has a molecular weight of approximately 460,000 in the absence of bound metals, and in nature one molecule of protein may bind as many as 4500 ferric atoms. Such a high binding capacity would permit a molar ratio of up to 1:4500 ferritin:metal. In contrast, the metal-binding protein, transferrin, having an approximate molecular weight of 77,000 binds only 2 ferric atoms per molecule, permitting a molar ratio of 1:2 transferrin:metal.

In general, the bifunctional chelators used in the present invention are capable of binding (chelating) one atom of metal cation per molecule of chelator, and in general will bind one molecule of protein per molecule of chelator. Thus, the molar ratio of chelator-protein conjugate to metal will generally be at least 1:1, protein conjugate:metal. It is possible for one protein molecule to bind more than one bifunctional chelator molecule, and thus increase the ratio of metal to protein; however, at least a 1:1 conjugate ratio is preferred.

In the radioactive compositions of the present invention, the metal-binding protein need not be saturated, i.e., fully occupied with radioactive metal. A given mass of protein may be complexed with radioactive metal to produce a radioactive composition having a molar ratio of protein to metal of 1 to less than or equal to the binding capacity of the metal-binding protein.

The pharmaceutical compositions of the present invention contain radioactive metals complexed with high molecular weight metal-binding proteins, in a physiologically acceptable carrier. Examples of suitable physiologically acceptable carriers include aqueous carriers such as phosphate buffered saline (PBS), glycols or saline. The pharmaceutical compositions may be administered to a patient for therapeutic treatments by methods known in the art, e.g., intravenously or by injection. For example, a ferritin-Ho-166 composition may be prepared in saline and injected into a joint for radiation synovectomy.

The quantity of the radioactive composition administered to the patient will depend upon several factors including the specific radionuclide, its specific activity and emissions, the particular type of therapeutic treatment, e.g., type of injection site, duration of therapy desired, and type of disease being treated, and the amount of radioactivity desired at the site of injection.

A therapeutic dosage of radioactivity is that which is sufficient when administered to a patient, to achieve the therapeutic radiation ablation result, for example, the amount sufficient, when injected into the synovium of a patient, to ablate the synovial membrane. In general, the therapeutic dosage will be that which delivers approximately 5 Gy to 1,500 Gy. A more preferred dosage is that which delivers from about 20 Gy to about 500 Gy to the site of injection. Gy is Greys wherein 1 Gy equals 100 rads.

The invention will be further clarified by a consideration of the following examples, which are intended to be purely exemplary of the present invention.

EXAMPLE 1

Preparation of Ferritin-Sm-153 by Metal Exchange

A 50 $\mu$l quantity of ferritin containing bound iron (100 mg/mL, MW 900,000) was added to a vial containing 150 $\mu$l of 0.1M sodium citrate with 10 $\mu$L of Sm-153 solution ($3 \times 10^{-4}$M in 0.1N HCl) at a pH of 7. This solution was heated for five minutes at 80° C. After heating, 100 $\mu$l of the solution was injected into a 10 cm long SEPHADEX TM G-50 gel filtration column (a polysaccharide dextran sold by Pharmacia) and eluted with water, collecting 10 drop fractions in a fraction collector. The amount of activity in each fraction was determined using an NaI-well scintillation counter.

The majority of the radioactivity eluted in an early fraction corresponding to protein-bound Sm-153. A smaller percentage of the radioactivity eluted more slowly and corresponded to a smaller molecule, e.g., Sm-153-citrate.

A volume of 100 $\mu$l of the radiolabeled protein (fraction No. 7) was injected into the synovium of the left knee joint of an anesthetized rabbit. A NaI gamma detector was placed above the injected knee joint and the Sm-153 gamma activity remaining in the synovium was determined in counts per minute over a period of 1.6 hours. This procedure was repeated with injection into in the synovium of the right knee of the same rabbit.

The results indicated almost no leakage of radioactivity from the synovium. After corrections for decay, a curve was obtained by plotting the activity as a function of time. The curve was assumed to be a straight line and calculated slopes of $-0.08$ and $-0.26$ counts per 30 seconds using at least squares method were obtained for the left and the right knees, respectively.

EXAMPLE 2

Radiolabeled Ferritin Prepared by Addition Through a Bifunctional Chelant

Into a vial was placed 1 mL of SmCl$_3$ solution ($3 \times 10^{-4}$M, in 0.1N HCl). To this was added $\mu$l of tracer Sm-153 ($3 \times 10^{-4}$M Sm in 0.1N HCl) solution and 10 $\mu$l of $\alpha$-aminophenyl-1,4,7,10-tetraazacyclododecane-1,4,7,10-tetraacetic acid (14.9 mg/mL). The pH was adjusted to 7.5 with NaOH and the mixture was heated for 30 minutes at 100° C. Free metal was removed from the solution by passing it through an ion exchange resin. The percent metal in the complex of the purified solution was determined by ion exchange chromatography to be 98%. To 150 $\mu$l of this resultant metal complex solution was added 2 $\mu$L of thiophosgene and 150 $\mu$L of CHCl$_3$. The solution was shaken for 30 minutes and then extracted with ether to remove the CHCl$_3$. Ion exchange chromatography was used to determine that the percent Sm in the resulting isothiocyanate complex was 98%.

A volume of 50 $\mu$l of ferritin containing bound iron (1000 mg/mL, MW 900,000) was placed into a vial and 150 $\mu$L of HEPES buffer (N-[2-hydroxyethyl]piperazine-N'-[2-ethane sulfonic acid]) was added (pH of 7.4). The pH was adjusted to 8 with NaOH and 100 $\mu$L of the bifunctional isothiocyanato-Sm-153 complex was added. The solutin was permitted to stand overnight. Gel permeation chromatography as described for Example 1 was used to isolate the radiolabeled protein fraction.

Injection of the resultant radiolabeled protein composition into the synovium of a knee of a rabbit was performed as described for Example 1. The data was recorded and calculated as described for Example 1 and a slope of −0.03 counts per 30 seconds was obtained, again showing little to no leakage of this formulation from the synovium of the rabbit.

EXAMPLE A

Comparison of Radiolabeled Compositions for Use in Radiation Synovectomy

Ferritin was iodinated using NaI-131 and 1,3,4,6-tetrachloro-3 α,6α-diphenylglycouril (TDPG), a mediator for protein iodination sold under the trademark "IODOGEN" by Pierce Chemical Company. A 1.4 mg quantity of TDPG was placed in a polypropylene tube and 1.4 mL of chloroform was added. Aliquots of 50 μL (20 μg) were placed into one-gram glass vials and left unstoppered until the tubes were dry. The prepared TDPG was stored frozen until use. A volume of 50 μL of ferritin (100 mg/mL, MW 900,000) was placed into a vial and 100 mL of 0.2M phosphate buffer (pH of 7.2) was added. This mixture was then added to a prepared TDPG tube and 200 μL of NaI-131 (959 μCi) was added. After standing 10 minutes, the iodinated solution was passed through a PD-10 column (G-25 gel permeation) and eluted with 0.01M sodium phosphate buffer. The protein-bound fraction (3.5 to 4.5 mL) was collected.

A rabbit was injected with the collected protein-bound composition and the data obtained and calculated in the same manner as described for Example 1. The retention slope calculated was −20.7 counts per 30 seconds indicating a significant loss of the iodinated radioactivity from the synovium.

The procedure described above was repeated to iodinate the antibody protein B-72.3 (approximate MW, 150,000) (D. Colcher et al. *Cancer Research* 48, 4597-5603 1988). The iodinated protein was injected into the synovium of a rabbit and the activity determined and calculated as described for Example 1. A calculated slope of −4.2 counts per 30 seconds was observed. When NaI-131 alone was injected into the synovium of the opposite leg, a calculated slope of −155.1 was observed.

These data indicate that the high molecular weight protein ferritin when radiolabeled with a bifunctional chelate (Example 2) or with natural metal adsorption (Example 1) remained in the synovium of the rabbit for a prolonged period of time as compared with iodinated ferritin or iodinated antibody protein (B-72.3), the iodinated proteins showing at least a 16 fold increase in the rate of leakage from the site of injection.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A method for the treatment of rheumatoid arthritis comprising injecting into the synovium of a subject in need of such treatment a therapeutically effective amount of a pharmaceutical composition comprising a metal-binding protein having a molecular weight of approximately greater than 50,000 and a therapeutic radionuclide bound to the protein, wherein the radionuclide is a beta-emitter with a half-life from about 2 hours to about 7 days.

2. A method for the treatment of rheumatoid arthritis comprising injecting into the synovium of a subject in need of such treatment a therapeutically effective amount of a pharmaceutical composition comprising a protein having a molecular weight of approximately greater than 50,000, a bifunctional chelator covalently attached to the protein, and a therapeutic radionuclide chelated to the bifunctional chelator, wherein the radionuclide is a beta-emitter having a half-life of about 2 hours to about 7 days.

3. The method of claim 1, wherein the protein has a molecular weight of approximately greater than 250,000.

4. The method of claim 3 wherein the protein is ferritin.

5. The method of claim 2 wherein the protein is transferrin.

6. The method of claim 2, wherein the bifunctional chelator contains a polyaminocarboxylate or polyaminophosphonate chelating moiety.

7. The method of claim 6 wherein the bifunctional chelator is selected from the group consisting of 1,3-propanediamine-N-(carboxy-propyl)-N,N',N'-trimethylenephosphonic acid, ethylenediamine-N-(4-aminophenethyl)-N,N',N',-trimethylenephosphonic acid, ethylenediaminetetramethylenephosphonic acid, 1-(carboxy)ethylenediaminetetramethylenephosphonic acid, 1-(4-aminobenzyl)ethylenediaminetetramethylenephosphonic acid, N''-(4-aminophenyl)-dipropylenetriamine-N',N',N''',N'''-tetramethylenephosphonic acid and N''-(4-aminophenethyl)-diethylenetriamine-N'N',N''',N'''-tetramethylenephosphonic acid.

8. The method of claim 6, wherein the bifunctional chelator contains a cyclic polyaminocarboxylate or polyaminophosphonate chelating moiety.

9. The method of claim 8, wherein the bifunctional chelator is selected from the group consisting of α-aminophenyl-1,4,7,10-tetraazacyclododecane-1,4,7,10-tetraacetic acid, substituted 1,4,7-tris-carboxymethyl-1,4,7,10-tetraazacyclododecane, 1,4,8,11-tetraazacyclotetra-decane-N,N',N'',N'''-tetraacetic acid, 2-(p-nitrobenzyl)-1,4,7,10-tetraazacyclododecane-N,N',N'',N'''-tetraacetic acid, α-[2-(4-aminophenyl)ethyl]-1,4,7,10-tetraazacyclododecane-1,4,7,10-tetraacetic acid, α-[2-(4-aminophenyl)ethyl]-1,4,7,10-tetraazacyclododecane-1-acetic-4,7,10-tris(methylacetic acid, α-(4-aminophenyl)-1,4,7,10-tetraazacyclododecane-1,4,7,10-tetraacetic acid, α-(5-amino-2-methoxyphenyl)-1,4,7,10-tetraazacylododecnae-1,4,7,10-tetraacetic acid, 1-[2-(4-aminophenyl)ethyl]-1,4,7,10-tetraazacyclododecnae-4,7,10-triacetic acid, 1,4,7,10-tetraazacyclododecane-N,N',N'',N'''-tetraacetic acid, 1,4,7,10-tetraazacyclotridecane-N,N'N'',N'''-tetraacetic acid, 1,4,8,11-tetraazacyclotetradecane-N,N'N'',N'''-tetraacetic acid, 1,5,9,13-tetraazacyclohexadecane-N,N'N'',N'''-tetraacetic acid, and 1,4,7,10-tetraazacyclododenace-1,4,7,10-tetramethylenephosphonic acid.

10. The method of claim 9 wherein the bifunctional chelator is α-aminophenyl-1,4,7,10-tetraazacyclododecane-1,4,7,10-tetraacetic acid.

11. The method of claim 9 wherein the bifunctional chelator is α-[2-(4-aminophenyl)ethyl]-1,4,7,10-tetraazacyclododecane-1-acetic-4,7,10-tris(methylacetic acid).

12. The method of claim 2, wherein the protein has a molecular weight of approximately greater than 250,000.

13. The method of claim 1, wherein said radionuclide is selected from the group consisting of Ho-166, Sm-153, Re-186, Rh-105, Lu-177, In-115 m, Dy-165, Sc-47 and Re-188.

14. The method of claim 2, wherein said radionuclide is selected from the group consisting of Ho-166, Sm-153, Re-186, Rh-105, Lu-177, In-115 m, Dy-165, Sc-47 and Re-188.

15. The method of claim 13, wherein said radionuclide is Sm-153 or Ho-166.

16. The method of claim 14, wherein said radionuclide is Sm-153 or Ho-166.

* * * * *